(12) United States Patent
Sgroi, Jr.

(10) Patent No.: US 10,345,165 B2
(45) Date of Patent: Jul. 9, 2019

(54) FORCE SENSOR FOR SURGICAL DEVICES

(71) Applicant: Covidien LP, Mansfield, MA (US)

(72) Inventor: Anthony Sgroi, Jr., Wallingford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 15/666,181

(22) Filed: Aug. 1, 2017

(65) Prior Publication Data

US 2018/0067004 A1 Mar. 8, 2018

Related U.S. Application Data

(60) Provisional application No. 62/384,878, filed on Sep. 8, 2016.

(51) Int. Cl.
*G01L 1/22* (2006.01)
*A61B 17/072* (2006.01)
(Continued)

(52) U.S. Cl.
CPC .......... *G01L 1/2287* (2013.01); *A61B 17/068* (2013.01); *A61B 17/07207* (2013.01); *A61B 17/115* (2013.01); *A61B 17/1155* (2013.01); *A61B 90/06* (2016.02); *G01L 1/2231* (2013.01); *G01L 1/2243* (2013.01); *G01L 1/26* (2013.01); *A61B 2017/07257* (2013.01); *A61B 2090/064* (2016.02); *A61B 2090/065* (2016.02); *A61B 2562/0261* (2013.01)

(58) Field of Classification Search
None
See application file for complete search history.

(56) References Cited

U.S. PATENT DOCUMENTS 4,420,652 A 12/1983 Ikeno
4,672,418 A 6/1987 Moran et al.
(Continued)

FOREIGN PATENT DOCUMENTS

DE 3913066 A1 11/1990
DE 4338788 A1 5/1994
(Continued)

OTHER PUBLICATIONS

Extended European Search Report corresponding to counterpart European Patent Appln. No. EP 17 18 9941.2 dated Feb. 7, 2018.

*Primary Examiner* — Nathaniel T Woodward (57) ABSTRACT

The present disclosure relates to force sensors and force sensor substrates for use with surgical devices. A force sensor includes a substrate, a plurality of sensing elements, a distal plate, and a pin block assembly. The substrate includes a proximal portion and a distal portion including a proximally-facing surface in fluid communication with a distal surface via an opening extending therebetween. The plurality of sensing elements are mounted on a sensing area of the distal surface of the substrate. The distal plate is welded to the distal surface of the substrate, hermetically sealing the plurality of sensing elements between the distal plate and the distal surface of the substrate. The pin block assembly is welded to the proximally-facing surface of the distal portion of the substrate, hermetically sealing distal ends of a plurality of conductive pins between the pin block assembly and the substrate.

20 Claims, 9 Drawing Sheets

(51) Int. Cl.
   *A61B 17/115* (2006.01)
   *A61B 17/068* (2006.01)
   *G01L 1/26* (2006.01)
   *A61B 90/00* (2016.01)

(56) References Cited

U.S. PATENT DOCUMENTS

| | | | |
|---|---|---|---|
| 5,041,943 A | 8/1991 | Ilardi et al. | |
| 5,223,741 A | 6/1993 | Bechtel et al. | |
| 5,280,413 A | 1/1994 | Pai | |
| 5,313,022 A | 5/1994 | Piroozmandi et al. | |
| 5,497,290 A | 3/1996 | Fukui et al. | |
| 5,807,378 A * | 9/1998 | Jensen | B25J 3/04 403/316 |
| 5,940,279 A | 8/1999 | Gademann et al. | |
| 6,320,128 B1 | 11/2001 | Glovatsky et al. | |
| 6,351,194 B2 | 2/2002 | Takahashi et al. | |
| 6,374,678 B1 * | 4/2002 | Masuda | G01L 19/0084 73/706 |
| 6,449,168 B1 | 9/2002 | Soderholm | |
| 6,845,664 B1 * | 1/2005 | Okojie | B81B 7/0061 257/433 |
| 7,000,484 B2 * | 2/2006 | Kurtz | G01L 5/161 73/796 |
| 7,898,074 B2 | 3/2011 | Eckhardt et al. | |
| 8,354,587 B2 | 1/2013 | Tappel et al. | |
| 8,666,505 B2 | 3/2014 | O'Brien et al. | |
| 9,442,131 B2 | 9/2016 | Hazel et al. | |
| 2003/0177839 A1 | 9/2003 | Tsukada et al. | |
| 2007/0151390 A1 * | 7/2007 | Blumenkranz | A61B 19/2203 74/490.06 |
| 2008/0041166 A1 * | 2/2008 | Kurtz | G01B 7/18 73/777 |
| 2009/0012556 A1 * | 1/2009 | Boudreaux | A61B 17/068 606/206 |
| 2009/0157092 A1 * | 6/2009 | Blumenkranz | G01L 1/246 606/130 |
| 2010/0087835 A1 * | 4/2010 | Blumenkranz | A61B 90/10 606/130 |
| 2010/0298843 A1 * | 11/2010 | Blumenkranz | A61B 34/30 606/130 |
| 2013/0324999 A1 * | 12/2013 | Price | A61B 17/32009 606/41 |
| 2015/0300895 A1 | 10/2015 | Matsudate et al. | |
| 2015/0374370 A1 | 12/2015 | Zergiebel et al. | |
| 2015/0374449 A1 | 12/2015 | Chowaniec et al. | |
| 2016/0296234 A1 | 10/2016 | Richard et al. | |
| 2016/0310134 A1 | 10/2016 | Contini et al. | |
| 2017/0086879 A1 | 3/2017 | Williams | |

FOREIGN PATENT DOCUMENTS

| | | | | |
|---|---|---|---|---|
| GB | 2465977 A * | 6/2010 | | G01L 1/00 |
| WO | 2009021827 A2 | 2/2009 | | |

* cited by examiner

FORCE SENSOR FOR SURGICAL DEVICES

CROSS-REFERENCE TO RELATED APPLICATIONS

This application claims the benefit of, and priority to, U.S. Provisional Patent Application Ser. No. 62/384,878, filed on Sep. 8, 2016, the entire contents of which are hereby incorporated herein by reference.

TECHNICAL FIELD

The present disclosure relates generally to surgical devices. More particularly, the present disclosure relates to force sensors for powered surgical devices.

BACKGROUND

Force sensors are known, and there are multiple methods of fabricating these types of sensors. In one method, sensors utilize bonded strain gauges adhered to a flexing substrate within a load path. For example, a simply supported steel beam that is used integral to a load path can have a strain gauge mounted on the beam. The strain gauge is incorporated in a Wheatstone Bridge Circuit configuration and includes an excitation voltage. The circuit is designed to be at balance before deflection (i.e., no load) and the circuit will have a resistance at zero load. During loading, the beam will deflect and the strain gauge will produce a resistance change. This resistance change is a signal that can be converted into a force value imposed on the beam using a signal condition. Depending on the type of configuration (e.g., a quarter bridge, a half bridge, a full bridge), the signal will vary and require calibration to obtain the actual force imposed.

Some strain gauges incorporate a thin plastic film with a bonded NiCr (nickel-chromium or nichrome) wire path embedded on the film. When the film is bonded to the beam and the beam is deflected, the NiCr wire will also be subjected to bending causing a deformation of the wire. The deformation of the wire will cause the above mentioned change in electrical resistance.

The flexing substrate must be configured to elastically deform in an elastic region. In the event that the substrate is subjected to permanent deformation, the sensing wire of the strain gauge will be constrained in the deformed state. This will result in inaccurate subsequent readings of the sensor.

Solder connections are typically utilized in a strain gauge circuit, with the wire path of the strain gauge terminating at a pair of solder pads. Other connections are also used, such as laser welding, mechanical forcing of wires to the contact pads, etc.

The solder connections are subject to possible failures if the connections are made in areas of high strain. Such a strain can cause high levels of deformation causing the solder connections to fatigue. Depending on the level of strain, this fatigue can cause failure of the solder pad resulting in a loss of electrical signal rendering the sensor unusable.

If alternate sensors are used, e.g., those fabricated using vapor deposition of brittle materials, this phenomena can become more problematic. Sensor fabricated using vapor deposition include depositing several layers of media to create the sensor. Typically, the first layer consists of a thin layer of glass deposited along a surface that will incorporate the sensing wire. The sensing wire is first deposited along the substrate as a full NiCr covering. A laser then etches away the NiCr until the desired wire path is created having a pair of solder pads forming a sensing element as described above with respect to the bonded strain gauge. Finally, a covering layer is used to prevent moisture ingress preventing shorts of the wire trace. The covering layer may be a cured epoxy or an RTV sealant (e.g., room temperature vulcanization silicone), or a vapor deposited glass with a region of glass etched away to gain access to the solder pads. This allows for the soldering of the wires or a flex cable to the sensor.

The configurations described above suffer from problems. One problem is the ability to load the substrate in an instrument. When utilizing glass along the substrate, the glass can crack when loaded. Another problem is premature failing due to large strains on the solder pads.

Load reading sensors have been used to perform functions in a surgical device, such as a surgical stapling instrument. By using a load reading sensor, the clamping, stapling, and cutting forces can be monitored and used to facilitate these various functions. The load reading sensor can be used to detect pre-set loads and cause the instrument to react to such a response. For example, during clamping of thick tissue, the load will rise to a pre-determined limit where the instrument can slow clamping to maintain the clamping force as the tissue relaxes. This allows for clamping of thick tissue without damage to such tissue (e.g., serosa tears). One such example is the firing of a circular stapler to create an anastomosis for a powered EEA device (e.g., End-to-End Anastomosis device). The intelligence of such a device is at a higher product cost compared to currently available disposable units and thus would benefit if such intelligent devices are reusable.

Unfortunately, reusable devices must be cleaned (e.g., disinfected) using high pH solutions and sterilized prior to subsequent uses. The most common method of sterilization is the use of autoclaving. Autoclaving utilizes high pressure superheated steam (e.g., 37 PSI @ 137° C. for 18 minutes). Such as environment is known to damage various electronic components and thus a need exists for sensors that can withstand high pH cleaning and sterilizations.

SUMMARY

According to an aspect of the present disclosure, a force sensor includes a substrate, a plurality of sensing elements, a distal plate, and a pin block assembly. The substrate includes a proximal portion and a distal portion. The distal portion includes a proximally-facing surface in fluid communication with a distal surface via an opening extending therebetween. The distal surface has a distal load contact area and a sensing area. The plurality of sensing elements are mounted on the sensing area of the distal surface of the substrate. The distal plate is welded to the distal surface of the substrate, hermetically sealing the plurality of sensing elements between the distal plate and the distal surface of the substrate. The pin block assembly includes a plurality of conductive pins and is welded to the proximally-facing surface of the distal portion of the substrate, hermetically sealing distal ends of the plurality of conductive pins between the pin block assembly and the substrate.

The plurality of sensing elements may be strain gauges. The proximal and distal portions of the substrate may be stepped relative to each other, and the proximally-facing surface of the distal portion may extend laterally from a side of the proximal portion. In embodiments, the substrate may include a central aperture defined through the proximal and distal portions of the substrate. In some embodiments, the distal surface of the substrate includes a distally extending flange extending around the central aperture of the substrate and the distal plate includes a substantially planar end wall and a proximally extending flange, and a space is defined between the end wall of the distal plate and the distal surface of the substrate.

In embodiments, the pin block assembly further includes a plurality of glass substrates and a pin block housing having a plurality of openings defined therethrough. Each pin of the plurality of conductive pins extends through one of the plurality of glass substrates which is disposed within an opening of the plurality of openings of the pin block housing. In some embodiments, the pin block housing is housed within a pin block cover, and the distal ends of the plurality of conductive pins are disposed within the pin block cover and electrically coupled to the plurality of sensing elements. In certain embodiments, proximal ends of the plurality of conductive pins of the pin block assembly extend proximally out of the pin block cover.

The distal surface of the substrate may include a cavity defined therein. The plurality of sensing elements may be disposed within the cavity and the distal plate may be welded to the distal surface of the substrate over the cavity. The substrate may include a relief cut formed between the proximal and distal portions of the substrate and/or a hole defined in a side surface of the substrate.

According to another aspect of the present disclosure, a surgical device includes a handle assembly, an end effector, and an adapter assembly selectively interconnecting the handle assembly and the end effector. The adapter assembly includes a connector housing, a trocar connection housing, and a force sensor disposed between the connector housing and the trocar connection housing. The force sensor includes a substrate, a plurality of sensing elements, a distal plate, and a pin block assembly. The substrate includes a proximal portion and a distal portion. The distal portion includes a proximally-facing surface in fluid communication with a distal surface via an opening extending therebetween. The distal surface has a distal load contact area and a sensing area. The plurality of sensing elements are mounted on the sensing area of the distal surface of the substrate. The distal plate is welded to the distal surface of the substrate, hermetically sealing the plurality of sensing elements between the distal plate and the distal surface of the substrate. The pin block assembly includes a plurality of conductive pins and is welded to the proximally-facing surface of the distal portion of the substrate, hermetically sealing distal ends of the plurality of conductive pins between the pin block assembly and the substrate.

The distal load contact area of the distal surface of the force sensor may interface with the connector housing, and the proximal portion of the force sensor may include a proximal surface having a proximal load contact area that interfaces with the trocar connection housing. The plurality of sensing elements of the force sensor may be strain gauges. In embodiments, the force sensor includes a central aperture defined through the proximal and distal portions of the substrate. In some embodiments, the distal surface of the distal portion of the force sensor includes a distally extending flange extending around the central aperture of the substrate and the distal plate includes a substantially planar end wall and a proximally extending flange, and a space is defined between the end wall of the distal plate and the distal surface of the substrate.

In embodiments, the pin block assembly of the force sensor further includes a plurality of glass substrates and a pin block housing having a plurality of openings defined therethrough. Each pin of the plurality of conductive pins extends through one of the plurality of glass substrates which is disposed within an opening of the plurality of openings of the pin block housing. In some embodiments, the pin block housing is housed within a pin block cover, and the distal ends of the plurality of conductive pins are disposed within the pin block cover and electrically coupled to the plurality of sensing elements. In certain embodiments, proximal ends of the plurality of conductive pins of the pin block assembly extend proximally out of the pin block cover.

The distal surface of the distal portion of the force sensor may include a cavity defined therein. The plurality of sensing elements may be disposed within the cavity and the distal plate may be welded to the distal surface of the substrate over the cavity.

Embodiments can include one or more of the following advantages:

The force sensors and substrates thereof may be configured to withstand large loading forces without disrupting the surface containing the sensing electronics (e.g., sensing elements or strain gauges, and their associated components).

The force sensors and substrates thereof may be configured to prevent tear propagation of protective conformal coatings and/or layers of sensing elements disposed thereon, and/or prevent surface micro-strain from damaging solder welds.

The force sensors and substrates thereof may be configured to withstand environmental stresses associated with autowashing and/or autoclaving, thereby rendering the force sensors more durable for reuse.

Other aspects, features, and advantages will be apparent from the description, drawings, and the claims.

BRIEF DESCRIPTION OF THE DRAWINGS

Various aspects of the present disclosure are described herein below with reference to the drawings, which are incorporated in and constitute a part of this specification, wherein.

DETAILED DESCRIPTION

Embodiments of the present disclosure are now described in detail with reference to the drawings in which like reference numerals designate identical or corresponding elements in each of the several views. Throughout this description, the term "proximal" refers to a portion of a device, or component thereof, that is closer to a hand of a user, and the term "distal" refers to a portion of the device, or component thereof, that is farther from the hand of the user.

Figure 1:
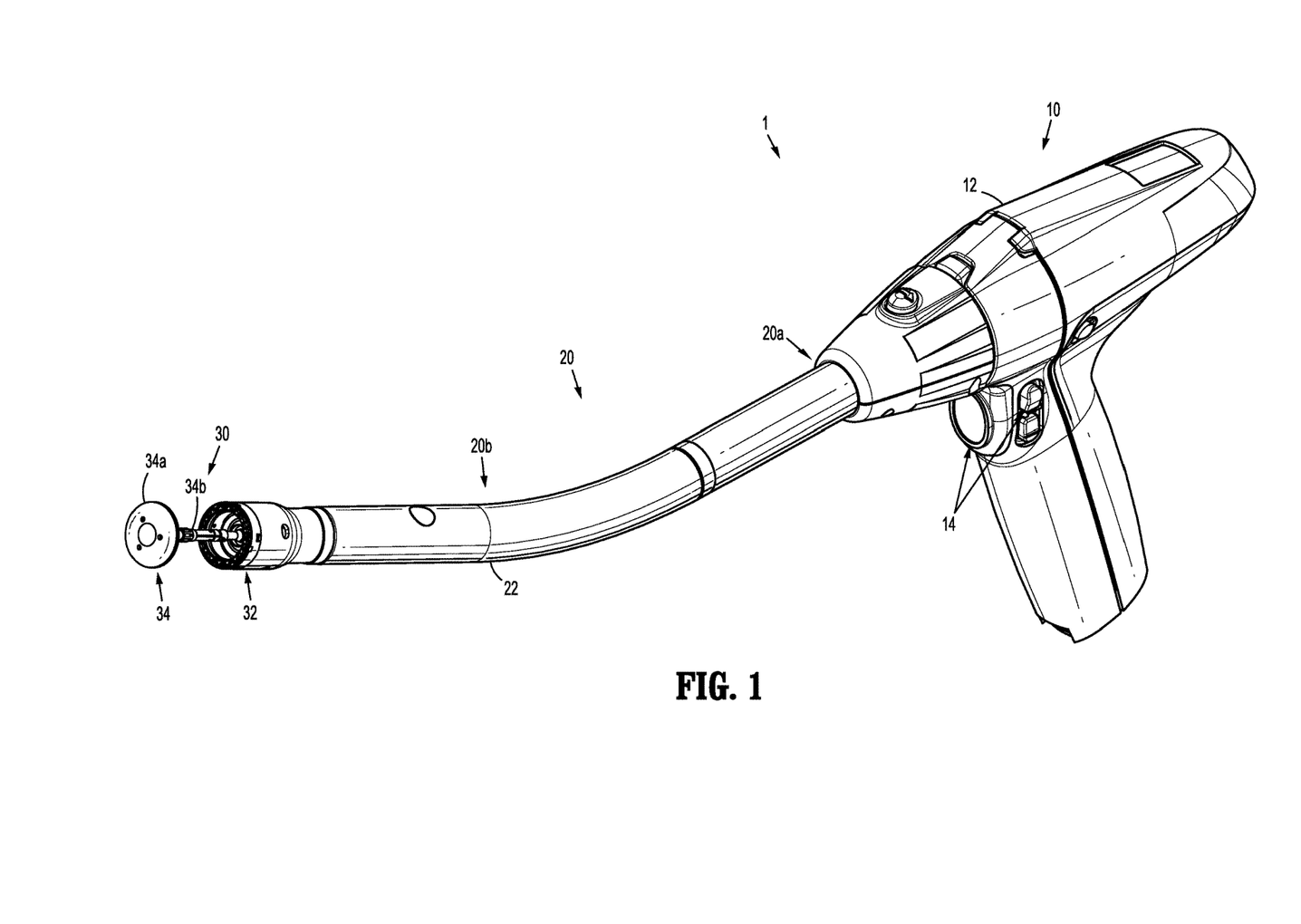
FIG. 1 is a perspective view of a surgical device in accordance with an embodiment of the present disclosure.

Turning now to FIG. 1, a surgical device 1, in accordance with an embodiment of the present disclosure, is in the form of a powered handheld electromechanical instrument, and includes a powered handle assembly 10, an adapter assembly 20, and a tool assembly or end effector 30 including a loading unit 32 having a plurality of staples (not shown) disposed therein and an anvil assembly 34 including an anvil head 34a and an anvil rod 34b. The powered handle assembly 10 is configured for selective connection with the adapter assembly 20 and, in turn, the adapter assembly 20 is configured for selective connection with the end effector 30.

While described and shown as including adapter assembly 20 and end effector 30, it should be understood that a variety of different adapter assemblies and end effectors may be utilized in the surgical device of the present disclosure. For a detailed description of the structure and function of exemplary surgical devices, reference may be made to commonly owned U.S. patent application Ser. No. 14/991, 157 ("the '157 application"), filed on Jan. 8, 2016, now U.S. Patent Appl. Pub. No. 2016/0296234, and U.S. patent application Ser. No. 15/096,399 ("the '399 application"), filed on Apr. 12, 2016, now U.S. Patent Appl. Pub. No. 2016/0310134, the entire contents of each of which are incorporated herein by reference.

With continued reference to FIG. 1, the handle assembly 10 includes a handle housing 12 housing a power-pack (not shown) configured to power and control various operations of the surgical device 1, and a plurality of actuators 14 (e.g., finger-actuated control buttons, knobs, toggles, slides, interfaces, and the like) for activating various functions of the surgical device 1. For a detailed description of an exemplary handle assembly, reference may be made to the '399 application, the entire contents of which was previously incorporated herein by reference.

Figure 2:
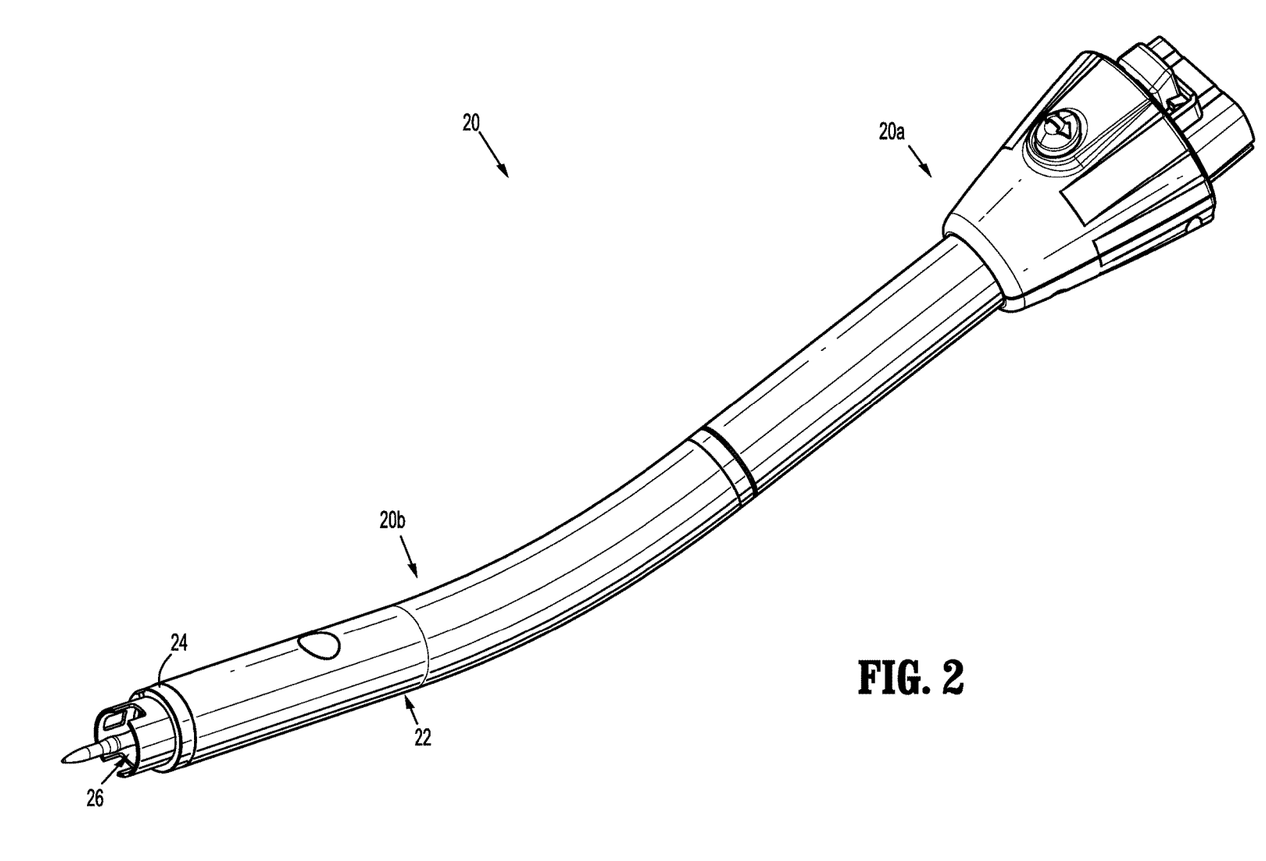
FIG. 2 is a perspective view of an adapter assembly of the surgical device of FIG. 1.

Referring now to FIG. 2, in conjunction with FIG. 1, the adapter assembly 20 includes a proximal portion 20a configured for operable connection to the handle assembly 10 (FIG. 1) and a distal portion 20b configured for operable connection to the end effector 30 (FIG. 1). The adapter assembly 20 includes an outer sleeve 22, and a connector housing 24 secured to a distal end of the outer sleeve 22. The connector housing 24 is configured to releasably secure an end effector, e.g., the end effector 30 (FIG. 1), to the adapter assembly 20.

The adapter assembly 20 will only further be described to the extent necessary to fully disclose the aspects of the present disclosure. For detailed description of an exemplary adapter assembly, reference may be made to the '157 application, the entire contents of which was previously incorporated herein by reference.

Figure 3A:
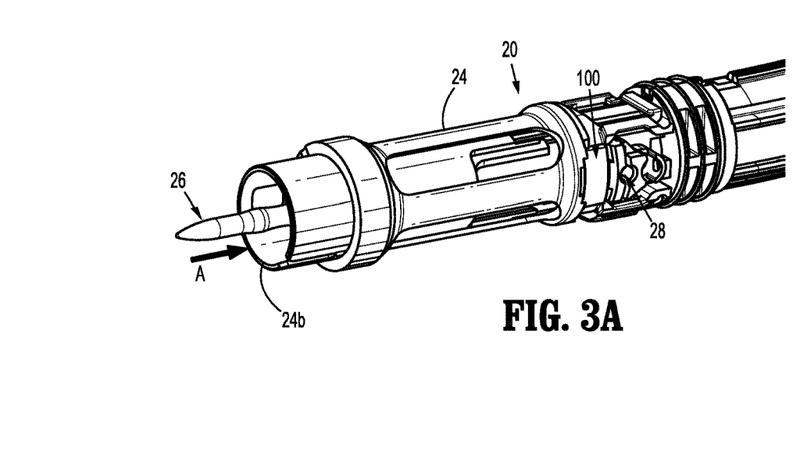
FIGS. 3A and 3B are perspective views of a distal end portion of the adapter assembly of FIGS. 1 and 2, with an outer sleeve of the adapter assembly removed.
Figure 3B:
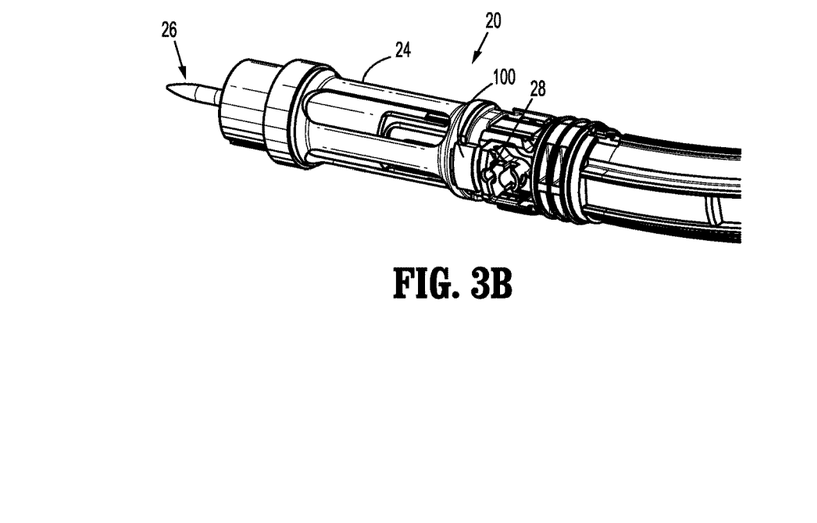
Figure 3C:
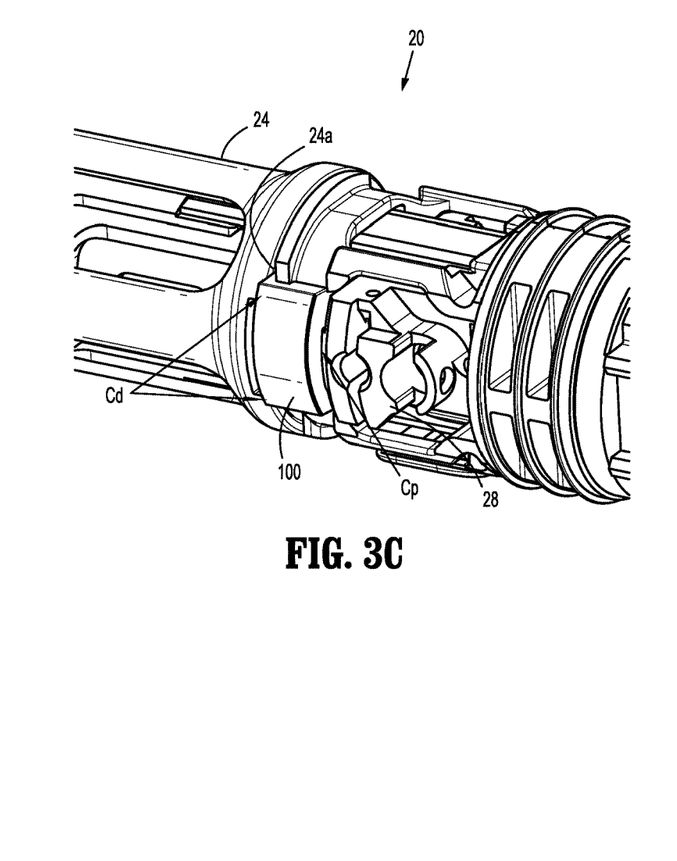
FIG. 3C is an enlarged perspective view of a part of the distal end portion of FIGS. 3A and 3B.

With reference now to FIGS. 3A-3C, the adapter assembly 20 further includes a trocar assembly 26 that extends through a central aperture 101 (FIG. 4B) of a force sensor 100 and a central aperture 29 (FIG. 4A) of a trocar connection housing 28. The trocar connection housing 28 releasably secures the trocar assembly 26 relative to the outer sleeve 22 (FIG. 2) of the adapter assembly 20. For a detailed description of an exemplary trocar connection housing, reference may be made to U.S. patent application Ser. No. 14/865,602 ("the '602 application"), filed on Sep. 25, 2015, now U.S. Patent Appl. Pub. No. 2017/0086879, the entire contents of which are incorporated herein by reference.

Figure 4A:
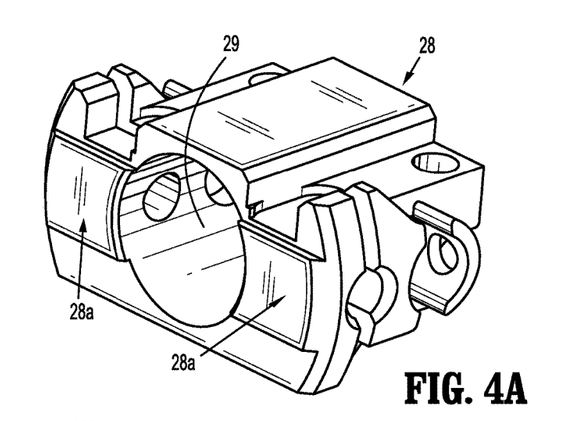
FIG. 4A is a perspective view of a trocar connection housing disposed in the distal end portion of the adapter assembly of FIGS. 3A-3C.
Figure 4B:
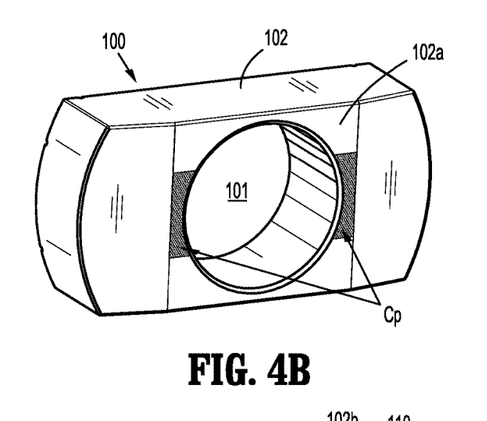
FIGS. 4B and 4C are perspective views of proximal and distal surfaces, respectively, of a substrate of a force sensor disposed in the distal end portion of the adapter assembly of FIGS. 3A-3C.
Figure 4C:
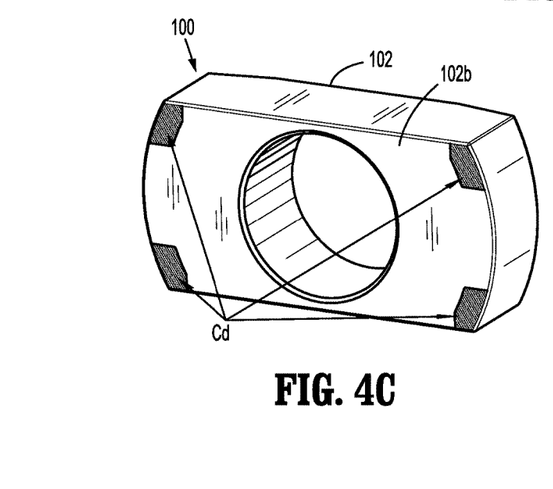

The force sensor 100 is disposed between the trocar connection housing 28 and the connector housing 24 of the adapter assembly 20, and is configured to measure forces along a load path. As shown in FIGS. 4A and 4B, in conjunction with FIG. 3C, the trocar connection housing 28 (FIG. 4A) includes a distal surface 28a which interfaces with, and loads a proximal surface 102a (FIG. 4B) of a body or substrate 102 of the force sensor 100 at proximal load contact areas "Cp". As shown in FIG. 4C, in conjunction with FIG. 3C, a proximal surface 24a (FIG. 3C) of the connector housing 24 defines a contact surface which loads a distal surface 102b of the substrate 102 of the force sensor 100 at distal load contact areas "Cd" (FIG. 4C). Thus, for example, as the anvil assembly 34 (FIG. 1) is approximated towards the loading unit 32 of the end effector 30 during clamping and/or stapling of tissue, the anvil head 34a applies uniform pressure in the direction of arrow "A" (FIG. 3A) against the distal end 24b of the connector housing 24 which, in turn, is transmitted to the distal load contact areas "Cd" of the force sensor 100.

Figure 5:
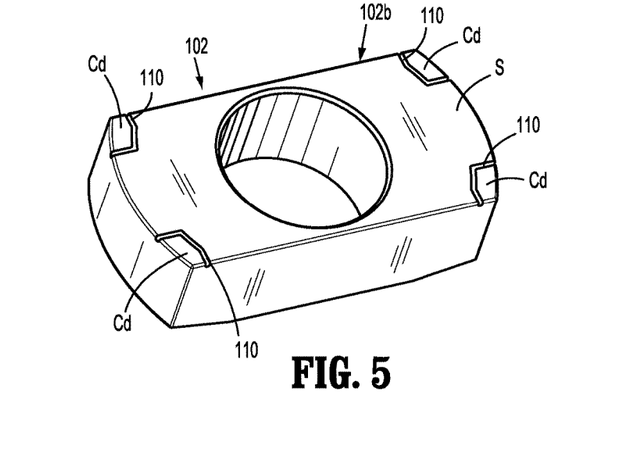
FIG. 5 is a perspective view of the substrate of the force sensor of FIGS. 3A-3C, 4B, and 4C.

With reference now to FIG. 5, the distal surface 102b of the substrate 102 is a generally planar surface having a plurality of grooves 110 defined therein. The plurality of grooves 110 provide an area of separate between the distal load contact area "Cd" and a sensing area "S" of the distal surface 102b of the substrate 102. The plurality of grooves 110 may be micro-trenches, relief cuts, among other depressed interruptions formed in the distal surface 102b. The plurality of grooves 110 may have a width of about 0.010 inches and a depth of about 0.010 inches, however, it should be understood that the width and depth may vary. It is contemplated that the width and/or depth of the plurality of grooves 110 can be any height and width such that the plurality of grooves 110 provide a region whereby a load can be applied to the adapter assembly 20 and/or the force sensor 100 without yielding a sensing substrate. It is further contemplated that the width and/or depth of the plurality of grooves 110 may be such so as to form a distinct loading surface independent of the sensing area "S". Moreover, while the plurality of grooves 110 are shown having a rectangular cross-sectional shape, it should be further understood that the shape of the plurality of grooves 110 may also vary.

The sensing area "S" of the distal surface 102b of the substrate 102 is a flat continuous surface onto which sensing elements 240 (FIG. 9B), e.g., strain gauges, are secured. The sensing area "S" of the substrate 102 is free of direct contact with the distal load contacting areas "Cd" via the plurality of grooves 110 thereby minimizing and/or preventing damage to the sensing element and/or associated components thereof (e.g., layers, coatings, circuitry, solder connections, etc.) as the sensing elements and/or other associated components are not subjected to the direct loading at the distal load contact areas "Cd."

In embodiments in which coatings are utilized to protect the circuitry and/or solder connections (not shown) disposed on the sensing area "S" of the substrate 102, the coatings may terminate at the plurality of grooves 110, without the need for masking processes, thereby minimizing or preventing tearing of the coatings in regions near the distal load contact areas "Cd" during loading of the force sensor 100.

In embodiments in which masking is desired, the plurality of grooves 110 allow for easier masking of the distal load contact areas "Cd" during fabrication of the force sensor 100. The plurality of grooves 100 provide break-away zones in which layers of the sensing elements and/or coatings thereon are forced to break thereby maintaining the integrity of the sensing area "S" of the substrate 102.

Figures 6A, 6B, 7A, 7B:
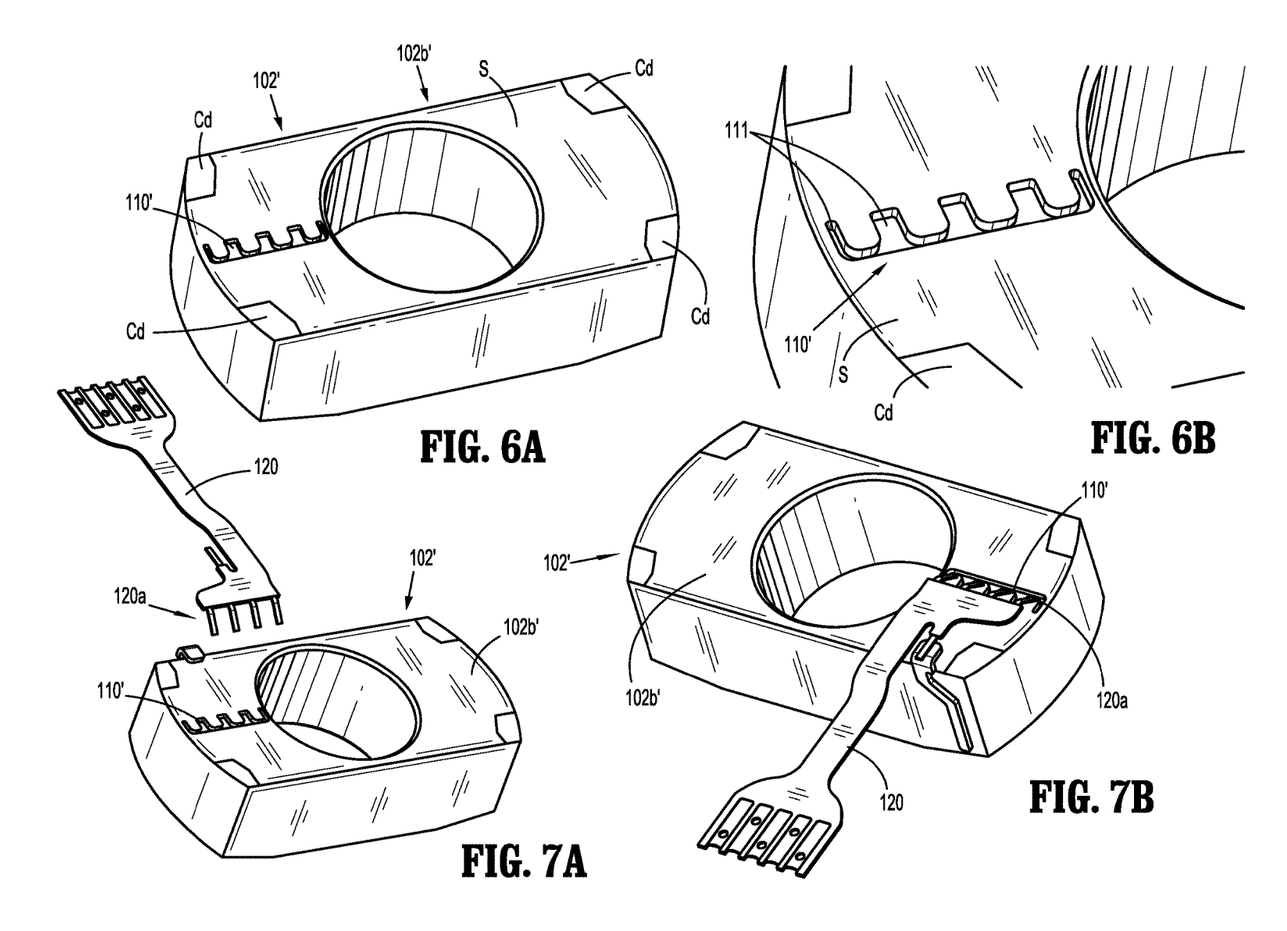
FIG. 6A is a perspective view of a substrate of a force sensor in accordance with another embodiment of the present disclosure.
FIG. 6B is a close-up view of a groove defined in the substrate of FIG. 6A.
FIGS. 7A and 7B are perspective views of the substrate of FIGS. 6A and 6B, including a flex cable.

Referring now to FIGS. 6A and 6B, another embodiment of a force sensor substrate 102' is illustrated. The substrate 102' is similar to substrate 102 and therefore described with respect to the differences therebetween.

The force sensor substrate 102' includes a proximal surface 102a (FIG. 4B) and a distal surface 102b' defining distal load contact areas "Cd" and sensing area "S". A groove 110' is formed in the sensing area "S" to isolate a desired solder contact surface in the sensing area "S" to create a localized region of reduced strain. The groove 110' includes a series of connected parallel cuts 111, each cut having a peninsula-like configuration. It should be understood, however, that one or more grooves 110' may be formed in a variety of arrangement, e.g., different shapes, depths, and/or widths, to transfer the strain beneath the distal surface 102b' of the substrate 102'.

As shown in FIGS. 7A and 7B, the geometry of the groove 110' corresponds to an end 120a of a flex cable 120, thereby reducing the strain, under load, at the surface of solder joints (not shown) formed between the end 120a of the flex cable 120 and the solder contact surface in the groove 110'. With the reduction of strain at distal surface 102b' of the substrate 102', the integrity of the solder connections are enhanced.

Figure 8A:
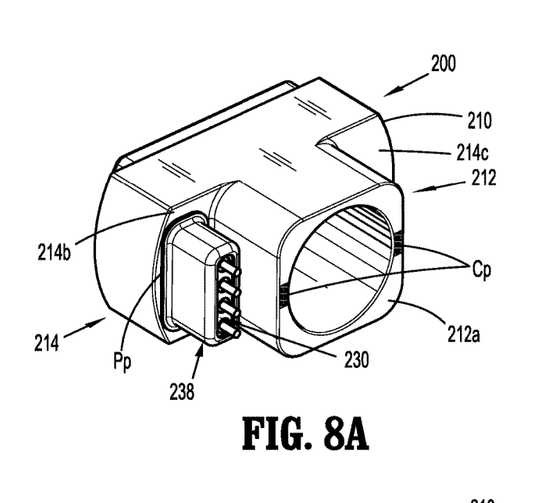
FIGS. 8A and 8B are perspective views of a force sensor in accordance with another embodiment of the present disclosure.
Figure 8B:
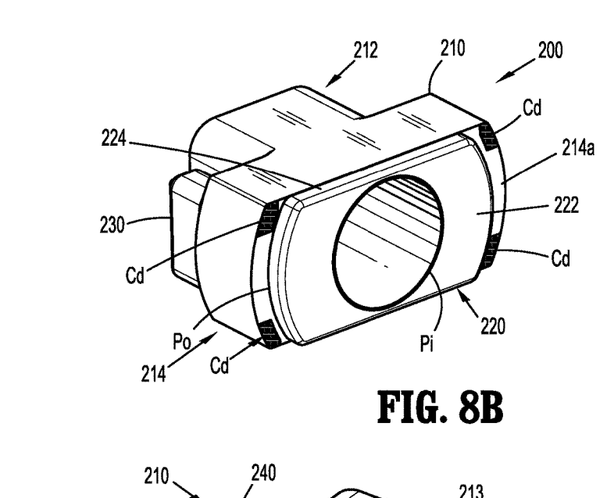

Referring now to FIGS. 8A and 8B, another embodiment of a force sensor is shown. The force sensor 200 includes a substrate 210, a distal plate 220, and a pin block assembly 230. The substrate 210 includes a proximal portion 212 and a distal portion 214 that are stepped relative to each other. The proximal portion 212 includes a proximal surface 212a that interfaces with the trocar connection housing 28 (FIG. 1), and the distal portion 214 includes a distal surface 214a that interfaces with the connector housing 24 (FIG. 1). The proximal and distal surfaces 212a, 214a are load bearing surfaces that allow the substrate 210 to compress when loaded by the surgical device 1 (FIG. 1), and include proximal and distal load contact areas "Cp" and "Cd," respectively, as described above with respect to force sensor 100. The distal portion 214 of the substrate 210 further includes first and second proximally-facing surfaces 214b, 214c that each extend laterally from opposed sides of the proximal portion 212 of the substrate 210.

Figure 9A:
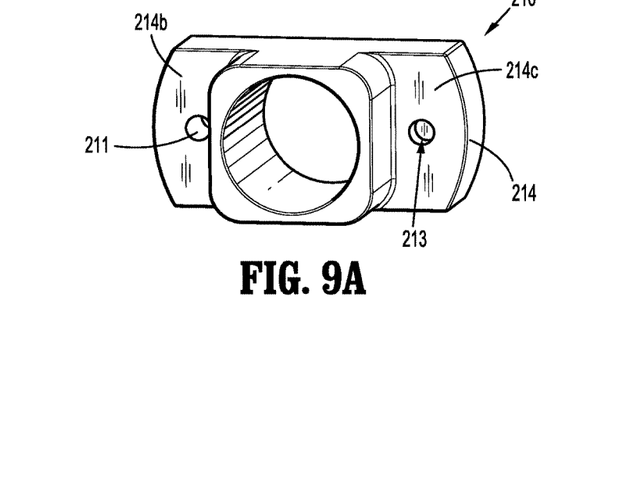
FIGS. 9A and 9B are perspective views of proximal and distal surfaces, respectively, of a substrate of the force sensor of FIGS. 8A and 8B.
Figure 9B:
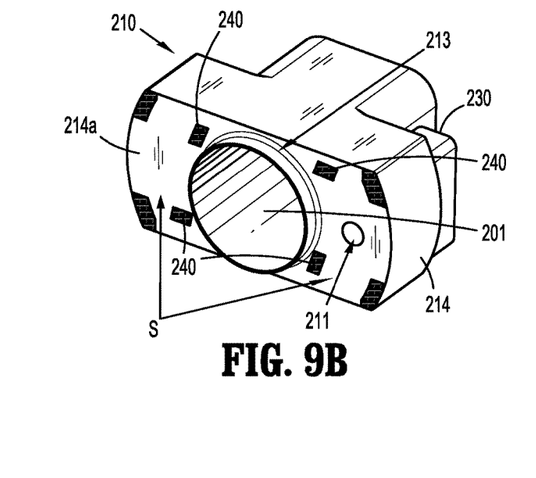
Figure 9C:
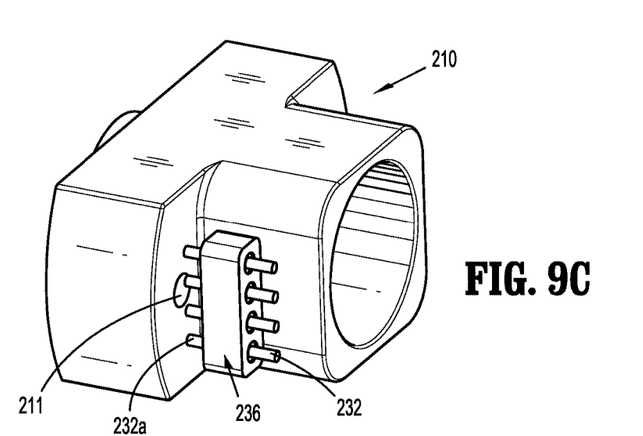
FIG. 9C is a side perspective view of the force sensor of FIGS. 8A and 8B, with a pin block cover of a pin block assembly removed.
Figure 10A:
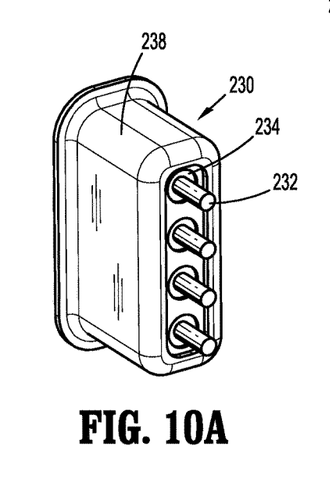
FIGS. 10A and 10B are perspective views of a pin block assembly of the force sensor of FIGS. 8A and 8B.
Figure 10B:
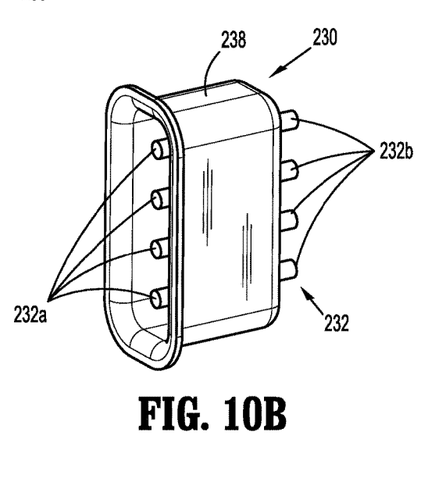
Figure 10C:
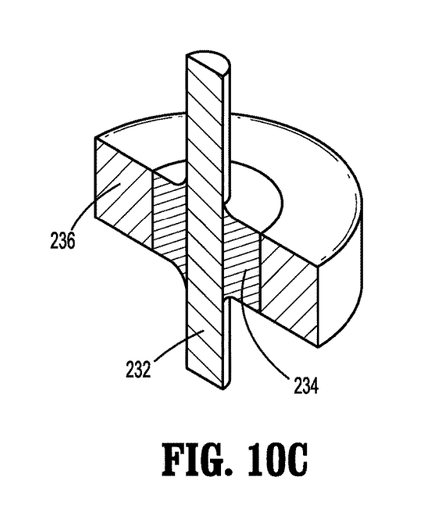
FIG. 10C is a schematic, cross-sectional illustration of a glass-to-metal pin transition in the pin block assembly of FIGS. 10A and 10B.

As shown in FIGS. 9A and 9B, the substrate 210 includes an opening 211 defined through the distal surface 214a and the first proximal-facing surface 214b of the distal portion 214, and aligned with the pin block assembly 230. Optionally, in some embodiments, as shown for example, in FIG. 9A, a hole 213 extending at least partially through a portion of the distal portion 214 of the substrate 210, in a location symmetrically opposed to the opening 211, may be included to equalize stresses on the substrate 210 during flexing of the substrate 210.

As shown in FIG. 9B, sensing elements 240 (e.g., strain gauges) are bonded to the sensing area "S" of the distal surface 214a of the substrate 210. The distal surface 214a further includes a distally extending flange 213 extending around a central aperture 201 defined through the substrate 210. As shown in FIG. 8B, the distal plate 220 includes a substantially planar end wall 222 and a proximally facing flange 224, such that when the distal plate 220 is mounted on the distal surface 214a of the substrate 210 a space is defined between the end wall 222 of the distal plate 220 and the distal surface 214a of the substrate 210, providing clearance for the sensing elements 240 and associated components (not shown). The distal plate 220 is welded, for example, by laser or electronic beam welding, to the distal surface 214a of the substrate 210 around the entirety of an outer perimeter "Po" and an inner perimeter "Pi" of the distal plate 220 to form a hermetic seal to protect the sensing elements 240 and associated components from the external environment. The distal plate 220 has a minimal thickness so as to bend and to allow for a responsive signal from the substrate 210 upon loading.

As shown in FIG. 9C-10C, the pin block assembly 230 includes a plurality of conductive pins 232, with each pin 232 extending through a glass substrate 234 disposed within a pin block housing 236 which is housed within a pin block cover 238. Distal ends 232a of the plurality of conductive pins 232 are disposed within the pin block cover 238, and proximal ends 232b of the plurality of conductive pins 232 extend proximally out through the pin block cover 238. Wires (not shown) are connected (e.g., soldered) to the sensing elements 240 (FIG. 9B) of the substrate 210 in a bridge configuration (e.g., a Wheatstone bridge), passed through the opening 211, and soldered to the distal ends 232a of the plurality of conductive pins 232 disposed within the pin block cover 238 so that electrical signals may exit the substrate 210 in order to supply power and read force responses from the force sensor 200.

As shown in FIG. 8A, the pin block cover 238 is welded, for example, by laser or electronic beam welding, to the first proximally-facing surface 214b of the substrate 210 around the entirety of an outer perimeter "Pp" of the pin block cover 238, such that the plurality of conductive pins 232 are hermetically sealed to the pin block assembly 230. Thus, the pin block assembly 230 allows for the connection of the wires (not shown) from the inside of the pin block assembly 230, through the opening 211 of the substrate 210, and to the sensing elements 240 (FIG. 9B) and associated components thereof, allowing the internal wires and electronics to be protected from the outside environment. Additionally, the hermetic sealing of the pin block assembly and distal plate, as well as the use of glass seals, allows the force sensor to withstand harsh environments (e.g., autowash and autoclave) so that the adapter assembly can be cleaned and/or sterilized for multiple uses.

Turning to FIGS. 11A-11D, another embodiment of a force sensor 200' is shown. The force sensor 200' is similar to force sensor 200 and therefore described with respect to the differences therebetween. The force sensor 200' includes a substrate 210', a distal plate 220', and a pin block assembly 230.

Figure 11A:
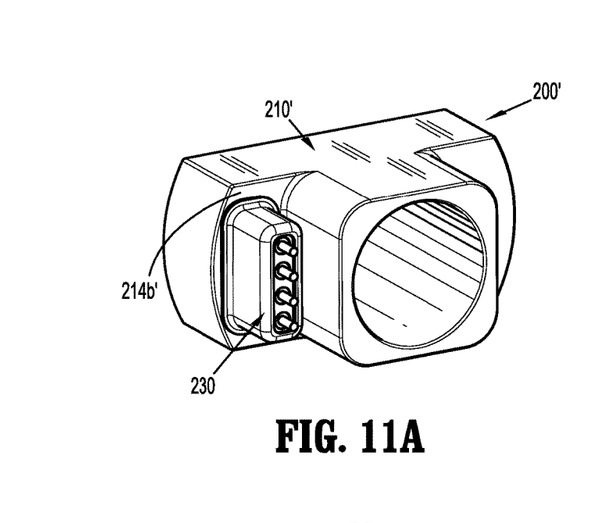
FIGS. 11A and 11B are perspective views of a force sensor in accordance with yet another embodiment of the present disclosure.
Figure 11B:
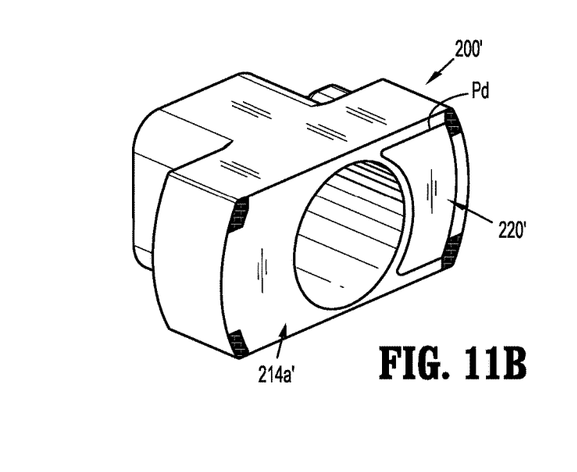
Figure 11C:
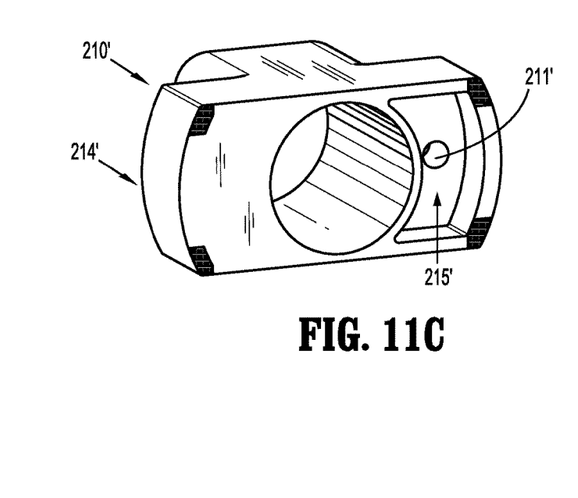
FIG. 11C is a perspective view of a substrate of the force sensor of FIGS. 11A and 11B, with a distal plate removed.
Figure 11D:
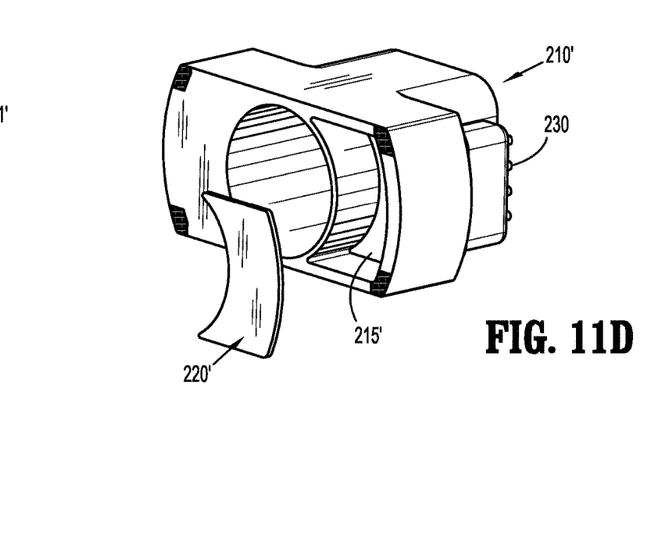
FIG. 11D is a perspective view of a substrate of the force sensor of FIGS. 11A and 11B, with a distal plate separated from the substrate.

The substrate 210' includes a distal portion 214' having a distal surface 214a' that is substantially planar, and defining a cavity 215' therein. The sensing elements 240 (FIG. 9B) are secured within the cavity 215' and the distal plate 220' is welded to the distal surface 214a' of the substrate 210' around the entire outer perimeter "Pd" of the distal plate 220' to form a hermetic seal to protect the sensing elements and associated components from the external environment. An opening 211' extends through a surface of the cavity 215' and a first proximally-facing surface 214b' of the distal portion 214' of the substrate 210'. Wires (not shown) that are soldered to the sensing elements 240 (FIG. 9B) extend through the opening 211' to the pin block assembly 230, as described above.

Figure 12A:
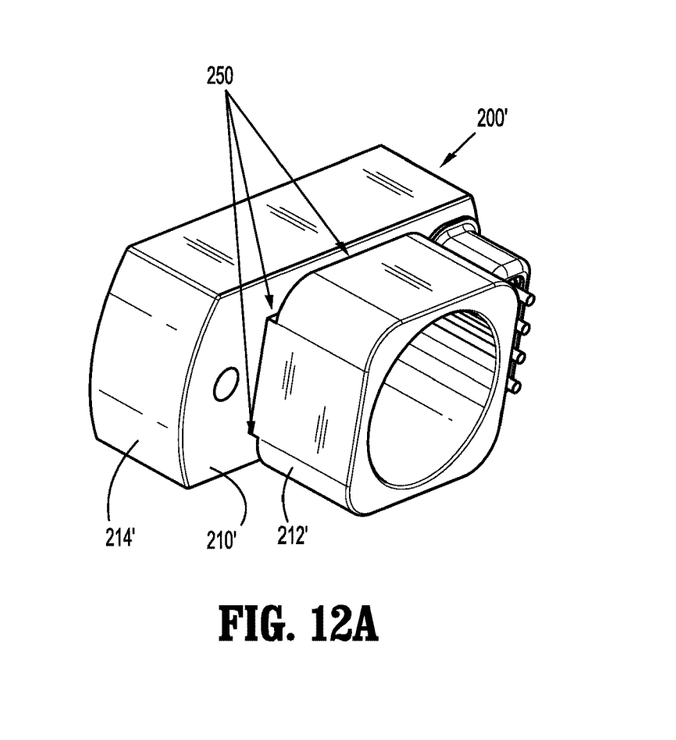
FIGS. 12A and 12B are perspective views of a force sensor including relief features in accordance with embodiments of the present disclosure.
Figure 12B:
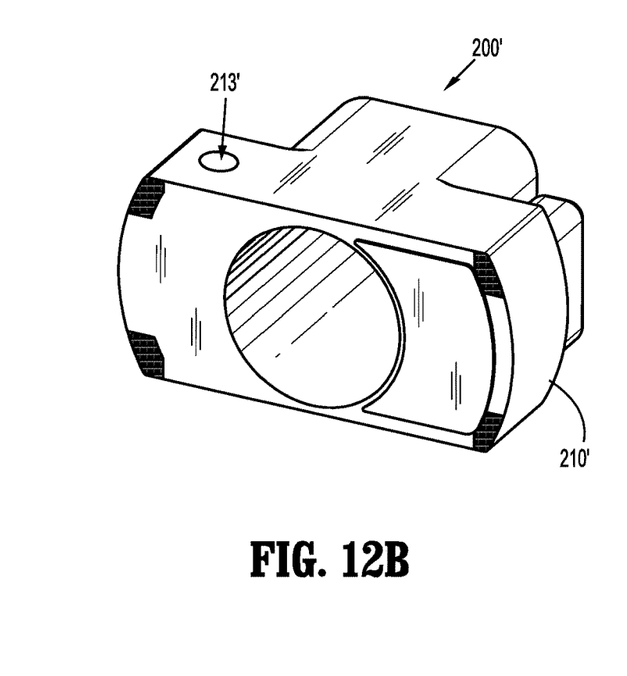

In embodiments in which more elongation (e.g., flex) is desired, the substrate of the force sensor may include one or more relief features to facilitate bending or to reduce stiffness. As shown, for example, in FIG. 12A, a series of relief cuts 250 are formed in the substrate 210' of the force sensor 200' between the proximal and distal portions 212' and 214'. As another example, as shown in FIG. 12B, a hole 213' is defined in a side surface of the substrate 210' of the force sensor 200'. The relief cuts 250 and/or holes 213' may be formed in a variety of sizes and shapes, such as, but not limited to circular, square, elliptical, trapezoidal, etc.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A force sensor comprising:
   a substrate including a proximal portion and a distal portion, the distal portion including a proximally-facing surface in fluid communication with a distal surface via an opening extending therebetween, the distal surface having a distal load contact area and a sensing area;
   a plurality of sensing elements mounted on the sensing area of the distal surface of the substrate;
   a distal plate welded to the distal surface of the distal portion of the substrate, the distal plate being disposed over the plurality of sensing elements and the opening defined through the distal portion of the substrate; and
   a pin block assembly including a plurality of conductive pins, the pin block assembly welded to the proximally-facing surface of the distal portion of the substrate and being disposed over the opening defined through the distal portion of the substrate, hermetically sealing distal ends of the plurality of conductive pins between the pin block assembly and the proximally-facing surface of the substrate and the plurality of sensing elements between the distal plate and the distal surface of the substrate, and allowing for connection of wires from inside the pin block assembly, through the opening, and to the plurality of sensing elements.

2. The force sensor according to claim 1, wherein the plurality of sensing elements are strain gauges.

3. The force sensor according to claim 1, wherein the proximal and distal portions of the substrate are stepped relative to each other, and the proximally-facing surface of the distal portion extends laterally from a side of the proximal portion.

4. The force sensor according to claim 1, wherein the substrate includes a central aperture defined through the proximal and distal portions of the substrate.

5. The force sensor according to claim 4, wherein the distal surface of the substrate includes a distally extending flange extending around the central aperture of the substrate and the distal plate includes a substantially planar end wall and a proximally extending flange defining an aperture therethrough coincident with the central aperture of the substrate, the distal plate welded to the distal surface of the substrate at an outer perimeter defined around the substantially planar end wall and an inner perimeter defined around the proximally extending flange to form a hermetic seal to protect the plurality of sensing elements, and wherein a space is defined between the end wall of the distal plate and the distal surface of the substrate.

6. The force sensor according to claim 1, wherein the pin block assembly further includes a plurality of glass substrates and a pin block housing having a plurality of openings defined therethrough, each pin of the plurality of conductive pins extending through one of the plurality of glass substrates which is disposed within an opening of the plurality of openings of the pin block housing.

7. The force sensor according to claim 6, wherein the pin block housing is housed within a pin block cover, the distal ends of the plurality of conductive pins disposed within the pin block cover and electrically coupled to the plurality of sensing elements.

8. The force sensor according to claim 7, wherein proximal ends of the plurality of conductive pins of the pin block assembly extend proximally out of the pin block cover.

9. The force sensor according to claim 1, wherein the distal surface of the substrate includes a cavity defined therein, the plurality of sensing elements disposed within the cavity and the distal plate welded to the distal surface of the substrate over the cavity.

10. The force sensor according to claim 1, wherein the substrate includes a relief cut formed in an outer surface of the substrate between the proximal and distal portions of the substrate.

11. The force sensor according to claim 1, wherein the substrate includes a hole defined in a side surface thereof.

12. A surgical device comprising:
   a handle assembly;
   an end effector; and
   an adapter assembly selectively interconnecting the handle assembly and the end effector, the adapter assembly including a connector housing, a trocar connection housing, and a force sensor disposed between the connector housing and the trocar connection housing, the force sensor including:
      a substrate including a proximal portion and a distal portion, the distal portion including a proximally-facing surface in fluid communication with a distal surface via an opening extending therebetween, the distal surface having a distal load contact area and a sensing area;

a plurality of sensing elements mounted on the sensing area of the distal surface of the substrate;

a distal plate welded to the distal surface of the distal portion of the substrate, the distal plate being disposed over the plurality of sensing elements and the opening defined through the distal portion of the substrate; and a pin block assembly including a plurality of conductive pins, the pin block assembly welded to the proximally-facing surface of the distal portion of the substrate and being disposed over the opening defined through the distal portion of the substrate, hermetically sealing distal ends of the plurality of conductive pins between the pin block assembly and the proximally-facing surface of the substrate and the plurality of sensing elements between the distal plate and the distal surface of the substrate, and allowing for connection of wires from inside the pin block assembly, through the opening, and to the plurality of sensing elements.

13. The surgical device according to claim 12, wherein the distal load contact area of the distal surface of the force sensor interfaces with the connector housing, and the proximal portion of the force sensor includes a proximal surface having a proximal load contact area that interfaces with the trocar connection housing.

14. The surgical device according to claim 12, wherein the plurality of sensing elements of the force sensor are strain gauges.

15. The surgical device according to claim 12, wherein the force sensor includes a central aperture defined through the proximal and distal portions of the substrate, and the adapter assembly includes a trocar assembly extending through the central aperture of the force sensor.

16. The surgical device according to claim 15, wherein the distal surface of the distal portion of the force sensor includes a distally extending flange extending around the central aperture of the substrate and the distal plate includes a substantially planar end wall and a proximally extending flange defining an aperture therethrough coincident with the central aperture of the substrate, the distal plate welded to the distal surface of the substrate at an outer perimeter defined around the substantially planar end wall and an inner perimeter defined around the proximally extending flange to form a hermetic seal to protect the plurality of sensing elements, and wherein a space is defined between the end wall of the distal plate and the distal surface of the substrate.

17. The surgical device according to claim 12, wherein the pin block assembly of the force sensor further includes a plurality of glass substrates and a pin block housing having a plurality of openings defined therethrough, each pin of the plurality of conductive pins extending through one of the plurality of glass substrates which is disposed within an opening of the plurality of openings of the pin block housing.

18. The surgical device according to claim 17, wherein the pin block housing is housed within a pin block cover, the distal ends of the plurality of conductive pins disposed within the pin block cover and electrically coupled to the plurality of sensing elements.

19. The surgical device according to claim 18, wherein proximal ends of the plurality of conductive pins of the pin block assembly extend proximally out of the pin block cover.

20. The surgical device according to claim 12, wherein the distal surface of the distal portion of the force sensor includes a cavity defined therein, the plurality of sensing elements disposed within the cavity and the distal plate welded to the distal surface of the substrate over the cavity.

* * * * *